United States Patent [19]

Fletcher et al.

[11] 3,995,960
[45] Dec. 7, 1976

[54] METHOD AND APPARATUS FOR BACKGROUND SIGNAL REDUCTION IN OPTO-ACOUSTIC ABSORPTION MEASUREMENT

[76] Inventors: James C. Fletcher, Administrator of the National Aeronautics and Space Administration, with respect to an invention of Lars-Göran Rosengren, Kungsbacka, Sweden

[22] Filed: July 25, 1975

[21] Appl. No.: 599,284

[52] U.S. Cl. ................................ 356/204; 250/343; 356/97; 356/201
[51] Int. Cl.² ...................... G01J 3/42; G01N 21/24
[58] Field of Search ............. 356/51, 97, 201, 204, 356/205, 206; 250/343, 345

[56] References Cited

UNITED STATES PATENTS 3,820,901    6/1974    Kreuzer ............................. 356/97

OTHER PUBLICATIONS

Delany, M. E., "The Optic-Acoustic Effect in Gases;" *Science Progress,* July 1959, vol. 47, No. 187, pp. 459–467.

*Primary Examiner*—John K. Corbin
*Assistant Examiner*—Richard A. Rosenberger
*Attorney, Agent, or Firm*—Monte F. Mott; Paul F. McCaul; John R. Manning

[57] ABSTRACT

The sensitivity of an opto-acoustic absorption detector is increased to make it possible to measure trace amounts of constituent gases (approaching 0.01 parts per billion) in a sample by creating a second beam radiation path through the sample cell identical to a first path except as to length, alternating the beam through the two paths and minimizing the detected pressure difference for the two paths while the beam wavelength is tuned away from the absorption lines of the sample. Then with the beam wavelength tuned to the absorption line of any constituent of interest, the pressure difference is a measure of trace amounts of the constituent. The same improved detector may also be used for measuring the absorption coefficient of known concentrations of absorbing gases.

10 Claims, 2 Drawing Figures

METHOD AND APPARATUS FOR BACKGROUND SIGNAL REDUCTION IN OPTO-ACOUSTIC ABSORPTION MEASUREMENT

ORIGIN OF INVENTION

The invention described herein was made in the performance of work under a NASA contract and is subject to the providions of Section 305 of the National Aeronautics and Space Act of 1958, Public Law 85-568 (72 Stat. 435; 42 USC 2457).

BACKGROUND OF THE INVENTION

This invention relates to opto-acoustic absorption detectors commonly referred to as spectrophones, and more particularly to a method and apparatus for measuring the concentrations of absorbing gases in a sample cell using opto-acoustic detection of absorption.

There is an increasing interest in detecting trace amounts (approaching 0.01 parts per billion) of atmospheric pollutant gases in an air sample. However, the residual background signal, such as that produced by the heating of the cell windows, limits the sensitivity of opto-acoustic absorption detectors. Terrence F. Deaton, David A. Depatie and Thomas W. Walker report their efforts to overcome this problem of sensitivity with a differential cell in a paper titled "Absorption Coefficient Measurements of Nitrous Oxide and Methane at DF Laser Wavelengths," Applied Physics Letters, Vol. 25, No. 6, 300–303 (1975). Two identical cells were used in tandem. Both were first filled with non-absorbing gas, and the pressure differential signal between the cells was then minimized while the laser beam was transmitted through both cells to "zero" the instrument. Absorption measurements were then made by filling one cell with a sample. The pressure differential signal between the two cells represents the absorption coefficient of the test gas. Residual pressures which are present as background signals due to absorption by the windows of the cell is effectively balanced out by this double cell arrangement, but it has the problem that extreme care must be exercised in filling both cells to the same pressure during the balancing procedure and during the measuring procedure. Still another approach to the problem referred to, but not discussed in their paper, is the development of a "windowless resonant cell" by David A. Depatie. The problem with that approach is said in that paper to be that "the pickup of ambient acoustic noise increases."

SUMMARY OF THE INVENTION

In accordance with the present invention, the residual background signal in an opto-acoustic pressure detector is reduced by alternately diverting a beam of light to a second path through a second pair of windows in a sample cell. The lengths of the two paths are significantly different. The beam intensity in the two paths is then adjusted through suitable means to minimize the detected pressure difference between the two paths while the beam wavelength is tuned away from the absorption lines of the sample in the cell, thereby reducing any residual background signal due to absorption pressure of the window material. When the beam wavelength is thereafter tuned to the absorption line of any trace constituent of a gas sample in the cell, the pressure difference between the two paths through the two cells is due only to absorption by the specific constituent of interest in the cell having a spectral line at the wavelength of the laser.

The novel features that are cnsidered characteristic of this invention are set forth with particularity in the appended claims. The invention will best be understood from the following description when read in connection with the accompanying drawings.

DESCRIPTION OF THE PREFERRED EMBODIMENTS

Figure 1:
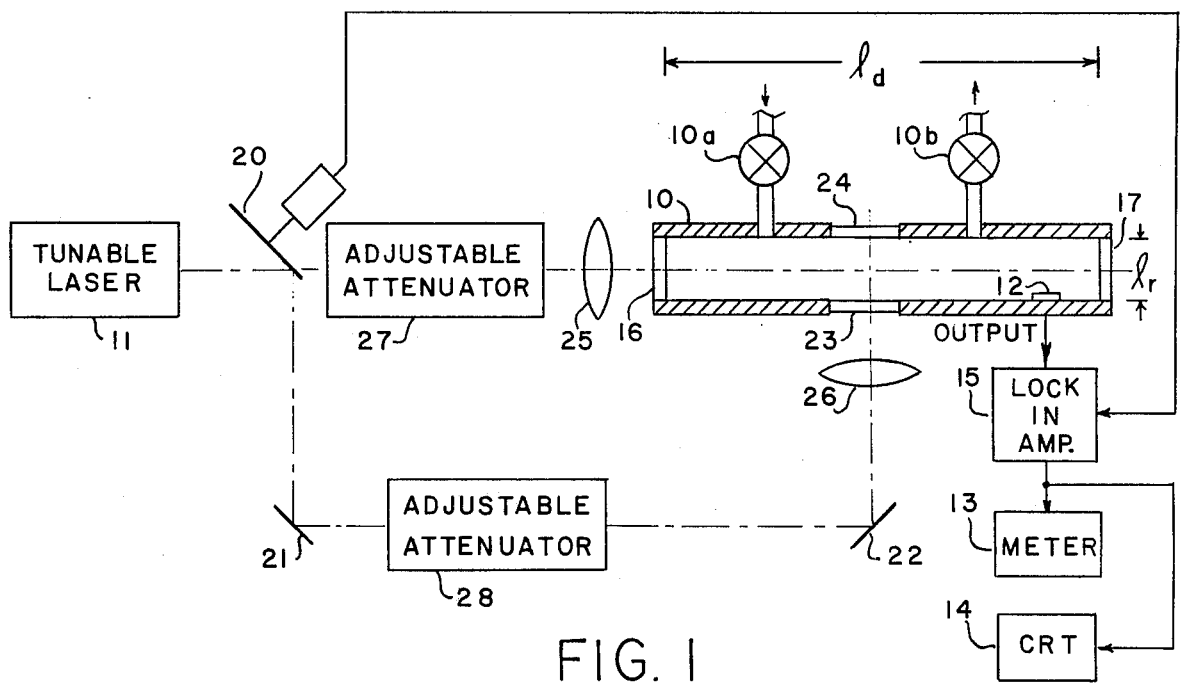
FIG. 1 is a schematic diagram of an exemplary embodiment of the present invention.

Referring now to FIG. 1, a sample cell 10 and tunable laser 11 is shown in an arrangement for opto-acoustic measurement of trace amounts (approaching 0.01 parts per billion) of atmospheric pollutant gases in an air sample. The cell is provided with an inlet valve 10a and an outlet valve 10b for sampling the air at some convenient pressure using a suitable pump (not shown) for first purging the cell while both valves are open, charging the cell with only valve 10a open and then closing the valve 10a when the desired static pressure is reached as measured (by means not shown).

The normal operation of an opto-acoustic detector requires tuning the laser wavelength to the absorption line of the molecules expected in the gas sample in the cell. The energy absorbed by the molecules increases the pressure in the cell. The increase in pressure is detected through a transducer 12, such as a capacitor microphone, and displayed on a meter 13 or on a cathode ray tube (CRT) 14 via an amplifier 15 implemented as a lock-in amplifier for sensitive, narrow bandwidth amplification in order to eliminate noise. That pressure is then a measure of the amount of the molecules, i.e., the concentration of the trace constituent of interest. The problem with this normal operation is that windows 16 and 17 for the laser beam path through the cell will absorb energy and cause an increase in pressure within the cell. The resulting background signal due to absorption losses in the cell windows is often large as compared to the absorption by trace constituents of a sample, making it impossible to use opto-acoustic techniques for detecting the presence of trace constituents.

To significantly improve the sensitivity of the opto-acoustic detector, a reflecting chopper 20 is employed to direct the laser beam via mirrors 21 and 22 through a second pair of windows 23 and 24. Lenses 25 and 26 are simply for focusing the laser beam through the cell windows. The chopper alternates the laser beam into the two paths, preferably with equal time through each path, although that is not necessary. By adjusting the light beam power through attenuators 27 and 28, it is possible to compensate for any time difference.

The alternate beam path through the second pair of windows is employed to balance out residual pressures due to absorption by the first pair of windows 16 and 17, although all windows are made of the same material and thickness, but that is not a requirement.

Figure 2:
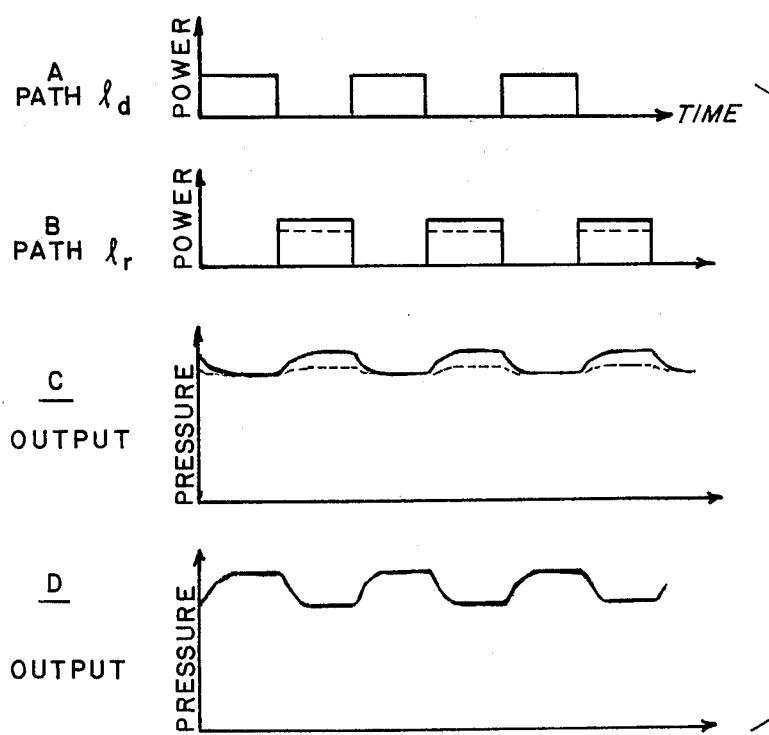
FIG. 2 is a diagram of waveforms useful in understanding the present invention.

It should be noted that the alternate (reflected) beam path has a length $l_r$ through the cell much shorter than the primary (direct) path which has a length $l_d$. Since the pressure, P, in the cell is proportional to the absorption coefficient, $\alpha$, and the path length, $l$, for a fixed cell volume, $v$, the direct path pressure ($P_d \approx k l_d$, where $k = \alpha/v$) will be much greater than the reflected path ($P_r = k l_r$). Consequently, as the laser beam is switched through the two paths, it modulates the cell pressure as shown in waveform C of FIG. 2. While the laser wavelength is turned off resonance of an absorption line of the sample gas, the attenuators 27 and 28 are adjusted so that the rms value of the first harmonic of the pressure difference (variations in amplitude of the waveform C) is minimum. The waveform displayed on the CRT will then be as shown by the dotted line waveform C in FIG. 2, assuming only the attenuator 28 is adjusted in this example. If both are adjusted, the dotted line waveform will have substantially the same form (approaching a straight line), but at a lower amplitude. Both attenuators may be conventional crystals for transmitting the polarized light of the laser with means for rotating the axis of the crystal relative to the axis of polarization of the light to attenuate the light transmitted.

In operation, the cell is charged with a sample of mixed gases and the laser wavelength is tuned away from the absorption line of the trace constituent suspected to be present in the sample. The relative beam intensity of the two transverse radiation paths is then adjusted to balance out the background signal due to absorption by the window material. That is done by operating on one or the other, or both, of the attenuators 27 and 28 in the beam paths, and observing the difference in pressure in the cell displayed on the CRT, as shown in waveforms C of FIG. 2. The solid line waveform C is indicative of the windows 23 and 24 absorbing more energy than the windows 16 and 17, but any unbalance may be opposite to that. By so adjusting the attenuators as to minimize the amplitude of any modulation present in that waveform C, any residual background in signal due to absorption by the windows 16 and 17 is balanced out.

Once the balancing procedure has been completed, the attenuators are locked in their adjusted position and the laser wavelength is tuned to the absorption lines of the constituent gases of interest. The pressure difference (amplitude of modulation) in the detector output displayed on the CRT as shown in waveform D is a measure of the amount (concentration) of a constituent associated with the wavelength of the beam. For example, if three pollutants are suspected of bein present in an air sample, the laser is tuned to the wavelength of the absorption line of each in sequence, noting at each wavelength the amplitude of the modulation on the detector output, i.e., on the output of the pressure transducer. The detected pressure amplitude is the measure of the amount of each pollutant present. Trace gas concentrations as low as 0.01 parts per million can be detected with this differential-path cell because it significantly reduces the background signal. The adjustment of the relative power in the two beam paths need not be readjusted if the power output of the laser varies. This is an important advantage. No special reference gas is required for this balancing procedure. That is another important advantage.

This differential-path cell may be used in situ for air pollution monitoring because it is rugged, simple, and occupies minimal space. It may also be used to equal advantage in a laboratory for measuring the concentration of each gas in a mixture of known gases, or for measuring absorption coefficients of known gas samples.

Although particular embodiments of the invention have been described and illustrated herein, it is recognized that modifications and equivalents may readily occur to those skilled in the art. For example, both sets of windows could be set at Brewster's angle to minimize reflection of light by the window material, particularly reflection of light from inside surfaces back through the sample in the cell. Use of Brewster's angle will, of course, permit arrangements for the two light paths other than at right angles to each other. Also light sources other than lasers could be used, but for sensitivity on the order of 0.01 parts per billion, a laser is required. Other suitable light sources might be ordinary white light sources directed in a beam through filters that pass a selected narrow band of wavelengths as required. Consequently, it is intended that the claims be interpreted to cover such modifications and equivalents.

I claim:

1. In an opto-acoustic absorption detector for measuring the concentration of constituent gases in a sample contained in a cell by transmitting a beam of light from a variable wavelength source through primary windows on opposite walls of said cell and producing as a measure of the concentration of said constituent, a signal proportional to any increase in pressure due to energy transfer to said sample through absorption of said beam at a selected wavelength on the absorption line of a constituent of said sample, apparatus for reducing any residual background signal produced as a result of an increase in pressure due to energy transfer to said sample through absorption by said windows comprising a second set of windows on opposite walls of said cell for passing a beam through said cell in a path of a length different from the path between said primary windows, means for alternately directing said beam of light through said primary windows and said second set of windows, means for adjusting the relative power of said beam in said two paths for minimum absorption pressure difference indicated by said signal when said beam is selected to be away from the absorption lines of constituents of said sample, and means for displaying the absorption pressure difference indicated by said signal for a selected wavelength of said beam as a measure of the concentration of a constituent in said sample when the wavelength of said beam selected is on the absorption line of said constituent.

2. Apparatus as defined by claim 1 wherein said means for alternately directing said beam comprises a reflecting chopper.

3. Apparatus as defined by claim 2 wherein said second set of windows are on the sides of said cell in a path normal to the path through said primary windows on the ends of said cell, and said reflecting chopper alternately passes said beam directly through one of said paths and reflects said beam 90° to a first 90° reflecting mirror and from there to a second 90° reflecting mirror which reflects the beam through the other of said paths.

4. Apparatus as defined in claim 3 wherein said primary windows and said second set of windows are made of the same material.

5. An opto-acoustic absorption detector capable of measuring concentrations of constituent gases of a sample in trace amounts approaching 0.01 parts per billion comprising means for producing a light beam of variable wavelength, a cell for containing said sample, means for detecting the pressure of said sample in said cell, primary windows in said cell for providing a first path for said beam through said cell, a second set of windows in said cell for providing a second path for said beam through said cell, said second path being of a length substantially different from the length of said first path, means for alternately directing said beam through said primary windows and said second set of windows, and means for adjusting the relative power of said beam directed through said primary windows and said second set of windows to minimize any difference detected by said pressure detecting means in the pressure of said sample in said cell due to transfer of energy by absorption of said beam while its wavelength is selected to be away from the absorption lines of said constituents, thereby balancing out any residual background signal from said pressure detecting means when the wavelengths selected thereafter are on the absorption lines of said constituents.

6. Apparatus as defined in claim 5 wherein said means for alternately directing said beam comprises a reflecting chopper.

7. Apparatus as defined in claim 6 wherein said second set of windows are on the sides of said cell in a path normal to the path through said primary windows on the ends of said cell, and said reflecting chopper alternately passes said beam directly through one of said paths and reflects said beam 90° to a first 90° reflecting mirror and from there to a second 90° reflecting mirror which reflects the beam through the other of said paths.

8. Apparatus as defined in claim 7 wherein said primary windows and said second set of windows are made of the same material.

9. In an opto-acoustic absorption detector for measuring the concentrations of constituent gases in a sample contained in a cell, a method for reducing any residual background signal due to absorption of energy by primary windows through which a beam of light is passed using a variable wavelength source of light comprising the steps of filling said cell with said sample, adjusting said beam of light to a wavelength away from the absorption lines of said constituents in said sample, alternately diverting said beam of light through a second set of windows disposed for passing the beam through said cell in a path distinct from the path between said primary windows, said second set of windows being spaced a distance apart significantly different from the distance between the primary windows, detecting any absorption pressure difference in said cell for the two paths, and adjusting the relative power of said beam in the two paths until the detected pressure difference is minimized, adjusting said beam of light to a particular wavelength on the absorption line of a constituent gas of interest in said sample, and detecting the absorption pressure difference in said cell for said beam at said particular wavelength as a measure of absorption by said constituent gas.

10. The method of claim 9 using the same material for both the primary windows and the second set of windows.

* * * * *